US006171598B1

(12) United States Patent
Wang et al.

(10) Patent No.: US 6,171,598 B1
(45) Date of Patent: Jan. 9, 2001

(54) GTP CYCLOHYDROLASE II (RIBA)

(75) Inventors: Min Wang, Blue Bell, PA (US); Judith M Ward, Dorking (GB); Richard Lloyd Warren, Blue Bell, PA (US); Richard Oakley Nicholas, Collegeville, PA (US); Leslie Marie Palmer, Audubon, PA (US); Julie M Pratt, Verona (IT); David Justin Charles Knowles, Boroughbridge (GB); Michael Arthur Lonetto, Collegeville, PA (US); Jeffrey Mooney, Limerick, PA (US); Michael Terence Black, Chester Springs, PA (US); Martin Karl Russell Burnham, Barto, PA (US); Christine Debouck, Wayne, PA (US); Jason Craig Fedon, Strafford, PA (US); John Edward Hodgson, Malvern, PA (US); Deborah Dee Jaworski, Norristown, PA (US); Raymond Winfield Reichard, Quakertown, PA (US); Martin Rosenberg, Royersford, PA (US); Christopher Michael Traini, Media, PA (US); Yi Yi Zhong, Audubon, PA (US)

(73) Assignees: SmithKline Beecham Corporation, Philadelphia, PA (US); SmithKline Beecham plc (GB)

( * ) Notice: Under 35 U.S.C. 154(b), the term of this patent shall be extended for 0 days.

(21) Appl. No.: 09/225,967

(22) Filed: Jan. 6, 1999

Related U.S. Application Data

(62) Division of application No. 08/977,554, filed on Nov. 25, 1997, now Pat. No. 5,891,672, which is a division of application No. PCT/US97/02318, filed on Feb. 19, 1997
(60) Provisional application No. 60/011,888, filed on Feb. 20, 1996.

(51) Int. Cl.$^7$ .................. A61K 38/50; A61K 39/085; C12N 9/14; C12N 9/78; C07K 14/31
(52) U.S. Cl. .................. 424/243.1; 424/190.1; 424/192.1; 435/195; 435/227; 514/12; 530/324; 530/350; 530/403
(58) Field of Search .................. 435/195, 227; 530/324, 350, 403; 514/12; 424/190.1, 192.1, 243.1

(56) References Cited

PUBLICATIONS

Fuller, et al., "Characterization of *Actinobacillus pleuropneumoniae* Riboflavin Biosynthesis Genes", Journal of Bacteriology, vol. 177, No. 24, pp. 7265–7270, (especially p. 7268), Dec., 1995.

*Primary Examiner*—Gary L. Kunz
*Assistant Examiner*—Stephen Gucker
(74) *Attorney, Agent, or Firm*—Edward R. Gimmi; Thomas S. Deibert; William T. King

(57) ABSTRACT

The invention provides ribA polypeptides and polynucleotides encoding ribA polypeptides and methods for producing such polypeptides by recombinant techniques. Also provided are methods for utilizing ribA polypeptides to screen for antibacterial compounds.

14 Claims, No Drawings

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
        (A) LENGTH: 1182 base pairs
        (B) TYPE: nucleic acid
        (C) STRANDEDNESS: double
        (D) TOPOLOGY: linear (xi) SEQUENCE DESCRIPTION: SEQ ID NO:1:

```
ATGCAATTCG ATAATATTGA CAGTGCTTTA ATGGCTTTAA AAAATGGAGA ACAATTATT      60

GTAGTAGATG ATGAGAATCG TGAAAATGAA GGTGATTTAG TAGCGGTTAC TGAATGGATG     120

AACGATAATA CCATTAATTT TATGGCGAAA GAAGCAAGGG GATTAATATG CGCACCAGTG     180

TCTAAAGATA TTGCACAACG TTTGGATTTG GTACAAATGG TTGATGATAA CTCCGACATC     240

TTTGGTACGC AATTTACAGT GAGTATTGAT CATGTAGATA CAACAACAGG AATTAGTGCT     300

TATGAACGTA CATTGACTGC CAAAAAGCTC ATTGATCCTA GTAGTGAAGC TAAAGATTTT     360

AATCGTCCTG GTCATTTATT TCCATTAGTA GCACAAGATA AAGGCGTATT AGCTAGAAAT     420

GGACACACAG AAGCGGCTGT TGATTTAGCT AAACTTACTG GTGCCAAGCC CGCTGGTGTC     480

ATTTGTGAGA TTATGAATGA TGACGGCACG ATGGCGAAAG GACAAGATTT ACAAAATTTT     540

AAAGAAAAAC ATCAATTAAA GATGATTACG ATTGATGATT TAATTGAATA TCGTAAAAAA     600

TTAGAACCAG AAATTGAATT TAAGGCAAAA GTGAAAATGC CTACAGATTT CGGAACATTT     660

GATATGTATG GTTTTAAAGC GACATACACA GATGAAGAGA TAGTTGTACT GACAAAAGGT     720

GCAATTCGAC AACATGAAAA TGTACGCTTA CATTCTGCGT GCCTTACAGG CGATATTTTC     780

CATAGTCAAC GTTGTGATTG TGGTGCTCAA CTTGAATCGT CTATGAAGTA TATCAATGAA     840

CATGGTGGCA TGATTATTTA TCTACCTCAA GAAGGTCGTG GCATAGGATT GTTAAACAAA     900

TTACGCGCAT ATGAATTAAT TGAGCAAGGA TATGATACAG TAACTGCAAA TTTAGCATTA     960

GGTTTTGATG AAGATTTACG AGATTATCAT ATTGCTGCAC AGATTTTAAA ATATTTTAAC    1020

ATCGAACATA TCAATTTATT AAGTAATAAT CCAAGTAAAT TTGAGGGATT AAAACAATAT    1080

GGCATTGATA TTGCAGAAAG AATTGAAGTT ATCGTACCAG AAACGGTACA TAATCATGAT    1140

TATATGGTAA CGAAAAAAAT AAAAATGGGT CATTTAATAT AG                       1182
```

(2) INFORMATION FOR SEQ ID NO:2:

(i) SEQUENCE CHARACTERISTICS:
        (A) LENGTH: 393 amino acids
        (B) TYPE: amino acid
        (C) STRANDEDNESS: single
        (D) TOPOLOGY: linear (xi) SEQUENCE DESCRIPTION: SEQ ID NO:2:

```
Met Gln Phe Asp Asn Ile Asp Ser Ala Leu Met Ala Leu Lys Asn Gly
 1               5                  10                  15

Glu Thr Ile Ile Val Val Asp Asp Glu Asn Arg Glu Asn Glu Gly Asp
                 20                  25                  30

Leu Val Ala Val Thr Glu Trp Met Asn Asp Asn Thr Ile Asn Phe Met
             35                  40                  45

Ala Lys Glu Ala Arg Gly Leu Ile Cys Ala Pro Val Ser Lys Asp Ile
 50                  55                  60

Ala Gln Arg Leu Asp Leu Val Gln Met Val Asp Asp Asn Ser Asp Ile
 65                  70                  75                  80

Phe Gly Thr Gln Phe Thr Val Ser Ile Asp His Val Asp Thr Thr Thr
                 85                  90                  95

Gly Ile Ser Ala Tyr Glu Arg Thr Leu Thr Ala Lys Lys Leu Ile Asp
                100                 105                 110

Pro Ser Ser Glu Ala Lys Asp Phe Asn Arg Pro Gly His Leu Phe Pro
                115                 120                 125

Leu Val Ala Gln Asp Lys Gly Val Leu Ala Arg Asn Gly His Thr Glu
    130                 135                 140

Ala Ala Val Asp Leu Ala Lys Leu Thr Gly Ala Lys Pro Ala Gly Val
145                 150                 155                 160

Ile Cys Glu Ile Met Asn Asp Asp Gly Thr Met Ala Lys Gly Gln Asp
                165                 170                 175

Leu Gln Asn Phe Lys Glu Lys His Gln Leu Lys Met Ile Thr Ile Asp
                180                 185                 190

Asp Leu Ile Glu Tyr Arg Lys Lys Leu Glu Pro Glu Ile Glu Phe Lys
                195                 200                 205

Ala Lys Val Lys Met Pro Thr Asp Phe Gly Thr Phe Asp Met Tyr Gly
    210                 215                 220

Phe Lys Ala Thr Tyr Thr Asp Glu Glu Ile Val Val Leu Thr Lys Gly
225                 230                 235                 240

Ala Ile Arg Gln His Glu Asn Val Arg Leu His Ser Ala Cys Leu Thr
                245                 250                 255

Gly Asp Ile Phe His Ser Gln Arg Cys Asp Cys Gly Ala Gln Leu Glu
                260                 265                 270

Ser Ser Met Lys Tyr Ile Asn Glu His Gly Gly Met Ile Ile Tyr Leu
    275                 280                 285

Pro Gln Glu Gly Arg Gly Ile Gly Leu Leu Asn Lys Leu Arg Ala Tyr
    290                 295                 300

Glu Leu Ile Glu Gln Gly Tyr Asp Thr Val Thr Ala Asn Leu Ala Leu
305                 310                 315                 320

Gly Phe Asp Glu Asp Leu Arg Asp Tyr His Ile Ala Ala Gln Ile Leu
                325                 330                 335

Lys Tyr Phe Asn Ile Glu His Ile Asn Leu Leu Ser Asn Asn Pro Ser
                340                 345                 350

Lys Phe Glu Gly Leu Lys Gln Tyr Gly Ile Asp Ile Ala Glu Arg Ile
    355                 360                 365
```

```
Glu Val Ile Val Pro Glu Thr Val His Asn His Asp Tyr Met Val Thr
    370                 375                 380
Lys Lys Ile Lys Met Gly His Leu Ile
385                 390
```

(2) INFORMATION FOR SEQ ID NO:3:

(i) SEQUENCE CHARACTERISTICS:
        (A) LENGTH: 461 base pairs
        (B) TYPE: nucleic acid
        (C) STRANDEDNESS: double
        (D) TOPOLOGY: linear (xi) SEQUENCE DESCRIPTION: SEQ ID NO:3:

```
AGCCGCTGGT GTCAATTTGT GAGATTATGA ATGATGACGG CACCGATGGC GAAAGGACCA      60

AGATTTACCA AAATTTTTAA AAGAAAAACA TCAATTAAAG ATGATTACGA TTGATGATTT     120

AATTGAATAT CGTAAAAAAT TAGAACCAGA AATTGAATTT AAGCCCAAAA GTGAAAATGC     180

CTACAGATTT CGGAACATTT GATATGTATG GTTTTAAAGC GACATACACA GATGAAGAGA     240

TAGTTGTACT GACAAAAGGT GCAATTCGAC AACATGAAAA TGTACGCTTA CATTCTGCGT     300

GCCTTACAGG CGATATTTTC CATAGTCAAC GTTGTGATTG TGGTGCTCAA CTTGAATCGT     360

CTATGAAGTA TATCAATGAA CATGGTGGCA TGATTATTTA TCTACCTCAA GAAGGTCGTG     420

GCATAGGATT GTTAAACAAA TTACGCTCGT GCCACGAGGA T                         461
```

(2) INFORMATION FOR SEQ ID NO:4:

(i) SEQUENCE CHARACTERISTICS:
        (A) LENGTH: 54 amino acids
        (B) TYPE: amino acid
        (C) STRANDEDNESS: single
        (D) TOPOLOGY: linear (xi) SEQUENCE DESCRIPTION: SEQ ID NO:4:

```
Arg His Arg Trp Arg Lys Asp Gln Asp Leu Pro Lys Phe Leu Lys Glu
1               5                   10                  15

Lys His Gln Leu Lys Met Ile Thr Ile Asp Asp Leu Ile Glu Tyr Arg
            20                  25                  30

Lys Lys Leu Glu Pro Glu Ile Glu Phe Lys Pro Lys Ser Glu Asn Ala
        35                  40                  45

Tyr Arg Phe Arg Asn Ile
    50
```

(2) INFORMATION FOR SEQ ID NO:5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:5:

```
ATATGCGCAC CAGTGTCTAA AG                                               22
```

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear -continued (xi) SEQUENCE DESCRIPTION: SEQ ID NO:6:

CATCGTGCCG TCATCATTCA T                                                    21

(2) INFORMATION FOR SEQ ID NO:7:

(i) SEQUENCE CHARACTERISTICS:
        (A) LENGTH: 3336 base pairs
        (B) TYPE: nucleic acid
        (C) STRANDEDNESS: double
        (D) TOPOLOGY: linear (xi) SEQUENCE DESCRIPTION: SEQ ID NO:7:

ATGGATTATG CGATTCAACT TGCAAATATG GTACAAGGTC AAACAGGTGT TAATCCACCC           60

GTTGGCGCTG TTGTAGTTAA TGAAGGTAGG ATTGTTGGTA TTGGTGCACA CTTGAGAAAA          120

GGTGACAAGC ATGCGGAGGT TCAAGCACTT GATATGGCAC AACAAAATGC TGAAGGTGCG          180

ACGATTTATA TTACGTTAGA GCCATGTAGT CATTTTGGTT CAACACCACC CTGTGTTAAC          240

AAAATTATTG ATTGTAAGAT AGCAAAAGTA GTATACGCAA CAAAAGACAA TTCGTTAGAC          300

ACACATGGTG ATGAGACGTT ACGGGCTCAC GGTATTGAGG TTGAATGCGT TGATGATGAA          360

CGGGCATCAC AATTATACCA AGACTTTTTT AAAGCAAAAG CAAAGCAACT GCCACAAATT          420

ACAGTGAAAG TATCTGCAAG TTTAGATGGT AAACAAGCGA ATGATAATGG ACAAAGTCAA          480

TGGATTACTA CAAAGAGGT TAAACAAGAT GTCTATAAGT TAAGACATCG ACACGACGCA           540

GTGTTAACTG GAAGACGTAC AGTTGAATTA GATGATCCAC AATATACTAC ACGTATTCAA          600

GATGGAAAAA ACCCTATAAA AGTAATATTG TCTAAGTCTG GAATATTCA TTTTAATCAG          660

CAAATTTATC AAGATGAATC AACACCAATT TGGATATATA CTGAAAATCC AAATTTAACA          720

AGCAATCAAA CACATATTGA AATTATTTAC TTGAAGTCTT GTGATTTAAC AACAATTCTT         780

CACAATTTAT ATAAAAGAGG AGTTGGAACT TTGCTAGTCG AGGCAGGTCC AACCACTACT          840

TCAGAATTCT CCATCTATTA TATAGATGAA TTTATTCTCT ATTATGCCCC GAAATTAATT          900

GGCGGATCTG GAAATTATCA ATTTTATCAA ACAAATGATG TGATTGAGAT ACCAGATGCG          960

AACCAATTTG AAATTGTTCA TTCCGAGTTA TTAAATCAAA ATGTTAAATT AACTTTACGA         1020

AAGAAGTGAT GATGCATGTT TACTGGCATC GTTGAAGAAA TAGGTGTCGT TAAAAGTGTT         1080

CAAATTCGTC AATCAGTCAG GACGATTGAA ATCGAAGCAC ATAAGATTAC GGCAGATATG         1140

CATATTGGTG ATTCCATCAG TGTTAATGGT GCATGTTTAA CAGTGATTGA TTTTGATCAG         1200

ACATCTTTTA CTGTTCAAGT AATTAAAAGC ACTGAAAATA AAACCTATTT AGCAGATGTT         1260

AAGCGACAAT CAGAAGTAAA TTTAGAGCGT GCCATGAGTG GTAACGGTAG GTTTGGTGGA         1320

CATTTTGTCC TCGGTCATGT AGATGAACTA GGAACAGTTT CAAAAATAAA TGAAACAGCC         1380

AATGCCAAAA TTATTACGAT TCAATGTAGC CAACATATTA ATAATCAGTT AGTTAAGCAA         1440

GGGTCTATTA CTGTGGATGG TGTAAGTCTA ACGGTATTTG ATAAGCATGA TAACAGTTTT         1500

GACATTCATC TTATTCCAGA AACGAGGCGT TCAACGATTT TATCATCCAA AAAATTAGGA         1560

GATAAAGTAC ATTTAGAAAC AGACGTTTTG TTTAAATATG TTGAAAATAT TTTAAATAAA         1620

GATAAAGACC AATTATCTGT AGATAAATTA AGAGCATTTG GTTTTAGGA GGGGTAGCAT          1680

GCAATTCGAT AATATTGACA GTGCTTTAAT GGCTTTAAAA AATGGAGAAA CAATTATTGT         1740

AGTAGATGAT GAGAATCGTG AAAATGAAGG TGATTTAGTA GCGGTTACTG AATGGATGAA         1800

CGATAATACC ATTAATTTTA TGGCGAAAGA AGCAAGGGGA TTAATATGCG CACCAGTGTC         1860

TAAAGATATT GCACAACGTT TGGATTTGGT ACAAATGGTT GATGATAACT CCGACATCTT         1920

-continued

```
TGGTACGCAA TTTACAGTGA GTATTGATCA TGTAGATACA ACAACAGGAA TTAGTGCTTA      1980

TGAACGTACA TTGACTGCCA AAAAGCTCAT TGATCCTAGT AGTGAAGCTA AAGATTTTAA      2040

TCGTCCTGGT CATTTATTTC CATTAGTAGC ACAAGATAAA GGCGTATTAG CTAGAAATGG      2100

ACACACAGAA GCGGCTGTTG ATTTAGCTAA ACTTACTGGT GCCAAGCCCG CTGGTGTCAT      2160

TTGTGAGATT ATGAATGATG ACGGCACGAT GGCGAAAGGA CAAGATTTAC AAAATTTTAA      2220

AGAAAAACAT CAATTAAAGA TGATTACGAT TGATGATTTA ATTGAATATC GTAAAAAATT      2280

AGAACCAGAA ATTGAATTTA AGGCAAAAGT GAAAATGCCT ACAGATTTCG GAACATTTGA      2340

TATGTATGGT TTTAAAGCGA CATACACAGA TGAAGAGATA GTTGTACTGA CAAAAGGTGC      2400

AATTCGACAA CATGAAAATG TACGCTTACA TTCTGCGTGC CTTACAGGCG ATATTTTCCA      2460

TAGTCAACGT TGTGATTGTG GTGCTCAACT TGAATCGTCT ATGAAGTATA TCAATGAACA      2520

TGGTGGCATG ATTATTTATC TACCTCAAGA AGGTCGTGGC ATAGGATTGT TAAACAAATT      2580

ACGCGCATAT GAATTAATTG AGCAAGGATA TGATACAGTA ACTGCAAATT TAGCATTAGG      2640

TTTTGATGAA GATTTACGAG ATTATCATAT TGCTGCACAG ATTTTAAAAT ATTTTAACAT      2700

CGAACATATC AATTTATTAA GTAATAATCC AAGTAAATTT GAGGGATTAA AACAATATGG      2760

CATTGATATT GCAGAAAGAA TTGAAGTTAT CGTACCAGAA ACGGTACATA ATCATGATTA      2820

TATGGTAACG AAAAAAATAA AAATGGGTCA TTTAATATAG GAGGACTTTA ACATGAATTT      2880

TGAAGGTAAA TTAATTGGAA AAGATTTGAA AGTTGCAATC GTAGTTAGTC GATTTAATGA      2940

TTTTATCACT GGAAGATTAC TTGAAGGTGC AAAAGATACT TTGATTCGAC ATGATGTTAA      3000

TGAAGACAAT ATTGATGTAG CATTTGTTCC TGGTGCGTTT GAAATTCCTT TAGTAGCTAA      3060

AAAATTAGCC TCATCAGGAA ATTATGATGC AATAATTACA TTAGGATGCG TAATTCGCGG      3120

TGCTACGTCT CATTATGATT ATGTTTGTAA TGAAGTGCGA AAGGTGTTTC TAAAGTAAAT      3180

GATCAAACTA ATGTACCAGT CATATTTGGT ATTTTAACGA CTGAAAGTAT TGAACAAGCT      3240

GTGGAAAGAG CAGGTACGAA AGCTGGTAAT AAAGGTGCCG AAGCAGCAGT AAGTGCAATT      3300

GAAATGGCTA ATTTATTAAA ATCTATAAAA GCATAG                               3336
```

GTP CYCLOHYDROLASE II (RIBA)

RELATED APPLICATIONS

This is a divisional of application Ser. No. 08/977,554, filed Nov. 25, 1997, now U.S. Pat. No. 5,891,672, and this application is a Div of PCT Application No. PCT/US97/02318, filed Feb. 19, 1997 and provisional application Serial No. 60/011,888, filed Feb. 20, 1996.

FIELD OF THE INVENTION

This invention relates to newly identified polynucleotides and polypeptides, and their production and uses, as well as their variants, agonists and antagonists, and their uses. In particular, the invention relates to novel polynucleotides and polypeptides of the GTP cyclohydrolase II family, hereinafter referred to as "ribA".

BACKGROUND OF THE INVENTION

It is particularly preferred to employ Staphylococcal genes and gene products as targets for the development of antibiotics. The Staphylococci make up a medically important genera of microbes. They are known to produce two types of disease, invasive and toxigenic. Invasive infections are characterized generally by abscess formation effecting both skin surfaces and deep tissues. Staphylococcus aureus is the second leading cause of bacteremia in cancer patients. Osteomyelitis, septic arthritis, septic thrombophlebitis and acute bacterial endocarditis are also relatively common. There are at least three clinical conditions resulting from the toxigenic properties of Staphylococci. The manifestation of these diseases result from the actions of exotoxins as opposed to tissue invasion and bacteremia. These conditions include: Staphylococcal food poisoning, scalded skin syndrome and toxic shock syndrome.

Riboflavin (vitamin B2) is a member of the B complex of vitamins which function as coenzymes in metabolic reactions. Riboflavin has two coenzyme forms, flavin mononucleotide (FMN) and flavin adenine dinucleotide (FAD) which act in oxidation-reduction reactions such as the cytochrome system of electron transport and the oxidative degradation of pyruvate, fatty acids and amino acids. The first committed step in the biosynthesis of riboflavin is the opening of the imidazole ring of GTP. In the presence of 3 $H_2O$ and $Mg^{++}$, the C-8 of GTP is released as formate accompanied by the release of pyrophosphate by the action of GTP cyclohyrolase II (GCH2; EC 3.5.4.25). This enzyme function is encoded by ribA in bacteria and rib1 in yeast species. Through a series of steps, involving 3,4-dihydroxy-2-butanone 4 phosphate synthase (ribA), 6,7-dimethyl-8-ribityllumazine synthase (ribH), riboflavin synthase (ribB), pyrimidine deaminase and pyrimidine reductase (ribG), enzymes encoded by genes within the riboflavin biosynthesis operon, riboflavin is formed. Because GCH2 catalyzes the first committed step in the biosynthesis of riboflavin (Richter G, et al. (1993) Biosynthesis of riboflavin: cloning, sequencing, mapping, and expression of the gene coding for GTP cyclohydrolase II in Escherichia coli. J Bacteriol. 175:4045–4051), is present in many pathogenic microorganisms, and since riboflavin biosynthesis has shown to be required for virulence in the swine pathogen Actinobacillus pleuropneumoniae (Fuller, T E, et al. (1996) A riboflavin auxotroph of Actinobacillus pleuropneumoniae is attenuated in swine. Infect. Immun. 64:4659–4664), it represents a broad spectrum antibacterial as well as antifungal target.

The frequency of Staphylococcus aureus infections has risen dramatically in the past few decades. This has been attributed to the emergence of multiply antibiotic resistant strains and an increasing population of people with weakened immune systems. It is no longer uncommon to isolate Staphylococcus aureus strains which are resistant to some or all of the standard antibiotics. This phenomenon has created a demand for both new anti-microbial agents, vaccines, and diagnostic tests for this organism.

Clearly, there exists a need for factors, such as the ribA embodiments of the invention, that have a present benefit of being useful to screen compounds for antibiotic activity. Such factors are also useful to determine their role in pathogenesis of infection, dysfunction and disease. There is also a need for identification and characterization of such factors and their antagonists and agonists to find ways to prevent, ameliorate or correct such infection, dysfunction and disease.

Certain of the polypeptides of the invention possess amino acid sequence homology to a known Bacillus amyloliquefaciens protein. (Swiss Prot. Accession no. P51695; GenBank Accession no. U27202; Perkins, J. B. et al., In: Bacillus subtilis and Other Gram-Positive Bacteria. Eds: Sonenshein, A. L. et al., 1993. American Society for Microbiology.)

SUMMARY OF THE INVENTION

It is an object of the invention to provide polypeptides that have been identified as novel ribA polypeptides by homology between the amino acid sequence set out in Table 1 [SEQ ID NO: 2 or 4] and a known amino acid sequence or sequences of other proteins such as Bacillus amyloliquefaciens protein.

It is a further object of the invention to provide polynucleotides that encode ribA polypeptides, particularly polynucleotides that encode the polypeptide herein designated ribA.

In a particularly preferred embodiment of the invention, the polynucleotide comprises a region encoding ribA polypeptides comprising a sequence set out in Table 1 [SEQ ID NO: 1, 3 or 7] which includes a full length gene, or a variant thereof.

In another particularly preferred embodiment of the invention, there is a novel ribA protein from Staphylococcus aureus comprising the amino acid sequence of Table 1 [SEQ ID NO:2 or 4], or a variant thereof.

As a further aspect of the invention, there are provided isolated nucleic acid molecules encoding ribA, particularly Staphylococcus aureus ribA, including mRNAs, cDNAs, genomic DNAs. Further embodiments of the invention include biologically, diagnostically, prophylactically, clinically or therapeutically useful variants thereof, and compositions comprising the same.

In accordance with another aspect of the invention, there is provided the use of a polynucleotide of the invention for therapeutic or prophylactic purposes, in particular genetic immunization. Among the particularly preferred embodiments of the invention are naturally occurring allelic variants of ribA and polypeptides encoded thereby.

As another aspect of the invention, there are provided novel polypeptides of Staphylococcus aureus referred to herein as ribA as well as biologically, diagnostically, prophylactically, clinically or therapeutically useful variants thereof, and compositions comprising the same.

Among the particularly preferred embodiments of the invention are variants of ribA polypeptide encoded by naturally occurring alleles of the ribA gene.

In a preferred embodiment of the invention, there are provided methods for producing the aforementioned ribA polypeptides.

In accordance with yet another aspect of the invention, there are provided inhibitors to such polypeptides, useful as antibacterial agents, including, for example, antibodies.

In accordance with certain preferred embodiments of the invention, there are provided products, compositions and methods for assessing ribA expression, treating disease, assaying genetic variation, and administering a ribA polypeptide or polynucleotide to an organism to raise an immunological response against a bacteria, especially a *Staphylococcus aureus* bacteria.

In accordance with certain preferred embodiments of this and other aspects of the invention, there are provided polynucleotides that hybridize to ribA polynucleotide sequences, particularly under stringent conditions.

In certain preferred embodiments of the invention, there are provided antibodies against ribA polypeptides.

In other embodiments of the invention, there are provided methods for identifying compounds which bind to or otherwise interact with and inhibit or activate an activity of a polypeptide or polynucleotide of the invention comprising: contacting a polypeptide or polynucleotide of the invention with a compound to be screened under conditions to permit binding to or other interaction between the compound and the polypeptide or polynucleotide to assess the binding to or other interaction with the compound, such binding or interaction being associated with a second component capable of providing a detectable signal in response to the binding or interaction of the polypeptide or polynucleotide with the compound; and determining whether the compound binds to or otherwise interacts with and activates or inhibits an activity of the polypeptide or polynucleotide by detecting the presence or absence of a signal generated from the binding or interaction of the compound with the polypeptide or polynucleotide.

In accordance with yet another aspect of the invention, there are provided ribA agonists and antagonists, preferably bacteriostatic or bactericidal agonists and antagonists.

In a further aspect of the invention, there are provided compositions comprising a ribA polynucleotide or a ribA polypeptide for administration to a cell or to a multicellular organism.

Various changes and modifications within the spirit and scope of the disclosed invention will become readily apparent to those skilled in the art from reading the following descriptions and from reading the other parts of the present disclosure.

DESCRIPTION OF THE INVENTION

The invention relates to novel ribA polypeptides and polynucleotides as described in greater detail below. In particular, the invention relates to polypeptides and polynucleotides of a novel ribA of *Staphylococcus aureus*, which is related by amino acid sequence homology to *Bacillus amyloliquefaciens* polypeptide. The invention relates especially to ribA having the nucleotide and amino acid sequences set out in Table 1 as SEQ ID NO: 1 and SEQ ID NO: 2 respectively.

TABLE 1 ribA Polynucleotide and Polypeptide Sequences (A) Sequences from *Staphylococcus aureus* ribA polynucleotide sequence [SEQ ID NO: 1].

5'-
ATGCAATTCGATAATATTGACAGTGCTTTAATGGCTTTAAAAAATGGAGAAACAATTATTGTAGTAGATG

ATGAGAATCG

TGAAAATGAAGGTGATTTAGTAGCGGTTACTGAATGGATGAACGATAATACCATTAATTTTATGGCGAAA

GAAGCAAGGG

GATTAATATGCGCACCAGTGTCTAAAGATATTGCACAACGTTTGGATTTGGTACAAATGGTTGATGATAA

CTCCGACATC

TTTGGTACGCAATTTACAGTGAGTATTGATCATGTAGATACAACAACAGGAATTAGTGCTTATGAACGTA

CATTGACTGC

CAAAAAGCTCATTGATCCTAGTAGTGAAGCTAAAGATTTTAATCGTCCTGGTCATTTATTTCCATTAGTA

GCACAAGATA

AAGGCGTATTAGCTAGAAATGGACACACAGAAGCGGCTGTTGATTTAGCTAAACTTACTGGTGCCAAGCC

CGCTGGTGTC

ATTTGTGAGATTATGAATGATGACGGCACGATGGCGAAAGGACAAGATTTACAAAATTTTAAAGAAAAAC

ATCAATTAAA

GATGATTACGATTGATGATTTAATTGAATATCGTAAAAAAATTAGAACCAGAAATTGAATTTAAGGCAAAA

GTGAAAATGC

CTACAGATTTCGGAACATTTGATATGTATGGTTTTAAAGCGACATACACAGATGAAGAGATAGTTGTACT

TABLE 1-continued ribA Polynucleotide and Polypeptide Sequences

GACAAAAGGT

GCAATTCGACAACATGAAAATGTACGCTTACATTCTGCGTGCCTTACAGGCGATATTTTCCATAGTCAAC

GTTGTGATTG

TGGTGCTCAACTTGAATCGTCTATGAAGTATATCAATGAACATGGTGGCATGATTATTTATCTACCTCAA

GAAGGTCGTG

GCATAGGATTGTTAAACAAATTACGCGCATATGAATTAATTGAGCAAGGATATGATACAGTAACTGCAAA

TTTAGCATTA

GGTTTTGATGAAGATTTACGAGATTATCATATTGCTGCACAGATTTTAAAATATTTTAACATCGAACATA

TCAATTTATT

AAGTAATAATCCAAGTAAATTTGAGGGATTAAAACAATATGGCATTGATATTGCAGAAAGAATTGAAGTT

ATCGTACCAG

AAACGGTACATAATCATGATTATATGGTAACGAAAAAAATAAAAATGGGTCATTTAATATAG-3'

(B) *Staphylococcus aureus* ribA polypeptide sequence deduced from
the polynucleotide sequence in this table [SEQ ID NO:2].

NH$_2$-

MQFDNIDSALMALKNGETIIVVDDENRENEGDLVAVTEWMNDNTINFMAKEARGLICAPVSKDIAQRLDL

VQMVDDNSDI

FGTQFTVSIDHVDTTTGISAYERTLTAKKLIDPSSEAKDFNRPGHLFPLVAQDKGVLARNGHTEAAVDLA

KLTGAKPAGV

ICEIMNDDGTMAKGQDLQNFKEKHQLKMITIDDLIEYRKKLEPEIEFKAKVKMPTDFGTFDMYGFKATYT

DEEIVVLTKG

AIRQHENVRLHSACLTGDIFHSQRCDCGAQLESSMKYINEHGGMIIYLPQEGRGIGLLNKLRAYELIEQG

YDTVTANLAL

GFDEDLRDYHIAAQILKYFNIEHINLLSNNPSKFEGLKQYGIDIAERIEVIVPETVHNHDYMVTKKIKMG

HLI-COOH (C) Polynucleotide sequences comprising *Staphylococcus aureus* ribA
ORF sequence [SEQ ID NO:3].

5'-

AGCCGCTGGTGTCAATTTGTGAGATTATGAATGATGACGGCACCGATGGCGAAAGGACCAAGATTTACCA

AAATTTTTAAAAGAAAAACATCAATTAAAGATGATTACGATTGATGATTTAATTGAATATCGTAAAAAAT

TAGAACCAGAAATTGAATTTAAGCCCAAAAGTGAAAATGCCTACAGATTTCGGAACATTTGATATGTATG

GTTTTAAAGCGACATACACAGATGAAGAGATAGTTGTACTGACAAAAGGTGCAATTCGACAACATGAAAA

TGTACGCTTACATTCTGCGTGCCTTACAGGCGATATTTTCCATAGTCAACGTTGTGATTGTGGTGCTCAA

CTTGAATCGTCTATGAAGTATATCAATGAACATGGTGGCATGATTATTTATCTACCTCAAGAAGGTCGTG

GCATAGGATTGTTAAACAAATTACGCTCGTGCCACGAGGAT

-3'

(D) *Staphylococcus aureus* ribA polypeptide sequence deduced from
the polynucleotide ORF sequence in this table [SEQ ID NO:4].

NH$_2$- RHRWRKDQDLPKFLKEKHQLKMITIDDLIEYRKKLEPEIEFKPKSENAYRFRNI-COOH

Deposited Materials

A deposit containing a *Staphylococcus aureus* WCUH 29 strain has been deposited with the National Collections of Industrial and Marine Bacteria Ltd. (herein "NCIMB"), 23 St. Machar Drive, Aberdeen AB2 1RY, Scotland on Sep. 11, 1995 and assigned NCIMB Deposit No. 40771, and referred to as *Staphylococcus aureus* WCUH29 on deposit. The *Staphylococcus aureus* strain deposit is referred to herein as "the deposited strain" or as "the DNA of the deposited strain."

The deposited strain contains the full length ribA gene. The sequence of the polynucleotides contained in the deposited strain, as well as the amino acid sequence of the polypeptide encoded thereby, are controlling in the event of any conflict with any description of sequences herein.

The deposit of the deposited strain has been made under the terms of the Budapest Treaty on the International Recognition of the Deposit of Micro-organisms for Purposes of Patent Procedure. The strain will be irrevocably and without restriction or condition released to the public upon the issuance of a patent. The deposited strain is provided merely as convenience to those of skill in the art and is not an admission that a deposit is required for enablement, such as that required under 35 U.S.C. §112.

A license may be required to make, use or sell the deposited strain, and compounds derived therefrom, and no such license is hereby granted.

One aspect of the invention there is provided an isolated nucleic acid molecule encoding a mature polypeptide expressible by the *Staphylococcus aureus* WCUH 29 strain contained in the deposited strain. Further provided by the invention are ribA nucleotide sequences of the DNA in the deposited strain and amino acid sequences encoded thereby. Also provided by the invention are ribA polypeptide sequences isolated from the deposited strain and amino acid sequences derived therefrom.

Polypeptides

The polypeptides of the invention include a polypeptide of Table 1 [SEQ ID NO:2 or 4] (in particular the mature polypeptide) as well as polypeptides and fragments, particularly those which have the biological activity of ribA, and also those which have at least 70% identity to a polypeptide of Table 1 [SEQ ID NO:1, 3 or 7] or the relevant portion, preferably at least 80% identity to a polypeptide of Table 1 [SEQ ID NO:2 or 4] and more preferably at least 90% similarity (more preferably at least 90% identity) to a polypeptide of Table 1 [SEQ ID NO:2 or 4] and still more preferably at least 95% similarity (still more preferably at least 95% identity) to a polypeptide of Table 1 [SEQ ID NO:2 or 4] and also include portions of such polypeptides with such portion of the polypeptide generally containing at least 30 amino acids and more preferably at least 50 amino acids.

The invention also includes polypeptides of the formula:

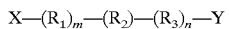

wherein, at the amino terminus, X is hydrogen, and at the carboxyl terminus, Y is hydrogen or a metal, $R_1$ and $R_3$ are any amino acid residue, m is an integer between 1 and 1000 or zero, n is an integer between 1 and 1000 or zero, and $R_2$ is an amino acid sequence of the invention, particularly an amino acid sequence selected from Table 1. In the formula above $R_2$ is oriented so that its amino terminal residue is at the left, bound to $R_1$, and its carboxy terminal residue is at the right, bound to $R_3$. Any stretch of amino acid residues denoted by either R group, where m and/or n is greater than 1, may be either a heteropolymer or a homopolymer, preferably a heteropolymer.

A fragment is a variant polypeptide having an amino acid sequence that entirely is the same as part but not all of the amino acid sequence of the aforementioned polypeptides. As with ribA polypeptides fragments may be "free-standing," or comprised within a larger polypeptide of which they form a part or region, most preferably as a single continuous region, a single larger polypeptide.

Preferred fragments include, for example, truncation polypeptides having a portion of an amino acid sequence of Table 1 [SEQ ID NO:2 or 4], or of variants thereof, such as a continuous series of residues that includes the amino terminus, or a continuous series of residues that includes the carboxyl terminus. Degradation forms of the polypeptides of the invention in a host cell, particularly a *Staphylococcus aureus*, are also preferred. Further preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions.

Also preferred are biologically active fragments which are those fragments that mediate activities of ribA, including those with a similar activity or an improved activity, or with a decreased undesirable activity. Also included are those fragments that are antigenic or immunogenic in an animal, especially in a human. Particularly preferred are fragments comprising receptors or domains of enzymes that confer a function essential for viability of *Staphylococcus aureus* or the ability to initiate, or maintain cause disease in an individual, particularly a human.

Variants that are fragments of the polypeptides of the invention may be employed for producing the corresponding fill-length polypeptide by peptide synthesis; therefore, these variants may be employed as intermediates for producing the full-length polypeptides of the invention.

In addition to the standard single and triple letter representations for amino acids, the term "X" or "Xaa" may also be used in describing certain polypeptides of the invention. "X" and "Xaa" mean that any of the twenty naturally occuring amino acids may appear at such a designated position in the polypeptide sequence.

Polynucleotides

Another aspect of the invention relates to isolated polynucleotides, including the full length gene, that encode the ribA polypeptide having a deduced amino acid sequence of Table 1 [SEQ ID NO:2 or 4] and polynucleotides closely related thereto and variants thereof.

Using the information provided herein, such as a polynucleotide sequence set out in Table 1 [SEQ ID NO:1, 3 or 7], a polynucleotide of the invention encoding ribA polypeptide may be obtained using standard cloning and screening methods, such as those for cloning and sequencing chromosomal DNA fragments from bacteria using *Staphylococcus aureus* WCUH 29 cells as starting material, followed by obtaining a full length clone. For example, to obtain a polynucleotide sequence of the invention, such as a sequence given in Table 1 [SEQ ID NO: 1, 3 or 7], typically a library of clones of chromosomal DNA of *Staphylococcus aureus* WCUH 29 in *E. coli* or some other suitable host is probed with a radiolabeled oligonucleotide, preferably a 17-mer or longer, derived from a partial sequence. Clones carrying DNA identical to that of the probe can then be distinguished using stringent conditions. By sequencing the individual clones thus identified with sequencing primers designed from the original sequence it is then possible to extend the sequence in both directions to determine the full gene sequence. Conveniently, such sequencing is performed using denatured double stranded DNA prepared from a plasmid clone. Suitable techniques are described by Maniatis, T., Fritsch, E. F. and Sambrook et al., *MOLECULAR CLONING, A LABORATORY MANUAL*, 2nd Ed.; Cold Spring Harbor Laboratory Press, Cold Spring Harbor, N.Y. (1989). (see in particular Screening By Hybridization 1.90 and Sequencing Denatured Double-Stranded DNA Templates 13.70). Illustrative of the invention, the polynucleotide set out in Table 1 [SEQ ID NO:1, 3 or 7] was discovered in a DNA library derived from *Staphylococcus aureus* WCUH 29.

The DNA sequence set out in Table 1 [SEQ ID NO:1, 3 or 7] contains an open reading frame encoding a protein having about the number of amino acid residues set forth in Table 1 [SEQ ID NO:2 or 4] with a deduced molecular weight that can be calculated using amino acid residue molecular weight values well known in the art. The polynucleotide of SEQ ID NO: 1, between nucleotide number 1 and the stop codon which begins at nucleotide number 1180 of SEQ ID NO:1, encodes the polypeptide of SEQ ID NO:2.

The ribA polypeptide of the invention is structurally related to other proteins of the GTP cyclohydrolase II family.

The invention provides a polynucleotide sequence identical over its entire length to a coding sequence in Table 1 [SEQ ID NO:1, 3 or 7]. Also provided by the invention is the coding sequence for the mature polypeptide or a fragment thereof, by itself as well as the coding sequence for the mature polypeptide or a fragment in reading frame with other coding sequence, such as those encoding a leader or secretory sequence, a pre-, or pro or prepro- protein sequence. The polynucleotide may also contain non-coding sequences, including for example, but not limited to non-coding 5' and 3' sequences, such as the transcribed, non-translated sequences, termination signals, ribosome binding sites, sequences that stabilize mRNA, introns, polyadenylation signals, and additional coding sequence which encode additional amino acids. For example, a marker sequence that facilitates purification of the fused polypeptide can be encoded. In certain embodiments of the invention, the marker sequence is a hexa-histidine peptide, as provided in the pQE vector (Qiagen, Inc.) and described in Gentz et al., *Proc. Natl. Acad. Sci., USA* 86: 821–824 (1989), or an HA tag (Wilson et al., *Cell* 37: 767 (1984). Polynucleotides of the invention also include, but are not limited to, polynucleotides comprising a structural gene and its naturally associated sequences that control gene expression.

A preferred embodiment of the invention is a polynucleotide of comprising nucleotide 1 to the nucleotide immediately upstream of or including nucleotide 1180 set forth in SEQ ID NO:1 of Table 1, both of which encode the ribA polypeptide.

The invention also includes polynucleotides of the formula:

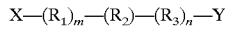

wherein, at the 5' end of the molecule, X is hydrogen, and at the 3' end of the molecule, Y is hydrogen or a metal, $R_1$ and $R_3$ is any nucleic acid residue, m is an integer between 1 and 3000 or zero, n is an integer between 1 and 3000 or zero, and $R_2$ is a nucleic acid sequence of the invention, particularly a nucleic acid sequence selected from Table 1.

In the polynucleotide formula above $R_2$ is oriented so that its 5' end residue is at the left, bound to $R_1$, and its 3' end residue is at the right, bound to $R_3$. Any stretch of nucleic acid residues denoted by either R group, where m and/or n is greater than 1, may be either a heteropolymer or a homopolymer, preferably a heteropolymer. In a preferred embodiment m and/or n is an integer between 1 and 1000.

It is most preferred that the polynucleotides of the inventions ire derived from *Staphylococcus aureus*, however, they may preferably be obtained from organisms of the same taxonomic genus. They may also be obtained, for example, from organisims of the same taxononic family or order.

The term "polynucleotide encoding a polypeptide" as used herein encompasses polynucleotides that include a sequence encoding a polypeptide of the invention, particularly a bacterial polypeptide and more particularly a polypeptide of the *Staphylococcus aureus* ribA having an amino acid sequence set out in Table 1 [SEQ ID NO:2 or 4]. The term also encompasses polynucleotides that include a single continuous region or discontinuous regions encoding the polypeptide (for example, interrupted by integrated phage or an insertion sequence or editing) together with additional regions, that also may contain coding and/or non-coding sequences.

The invention further relates to variants of the polynucleotides described herein that encode for variants of the polypeptide having a deduced amino acid sequence of Table 1 [SEQ ID NO:2 or 4]. Variants that are fragments of the polynucleotides of the invention may be used to synthesize full-length polynucleotides of the invention.

Further particularly preferred embodiments are polynucleotides encoding ribA variants, that have the amino acid sequence of ribA polypeptide of Table 1 [SEQ ID NO:2 or 4] in which several, a few, 5 to 10, 1 to 5, 1 to 3, 2, 1 or no amino acid residues are substituted, deleted or added, in any combination. Especially preferred among these are silent substitutions, additions and deletions, that do not alter the properties and activities of ribA.

Further preferred embodiments of the invention are polynucleotides that are at least 70% identical over their entire length to a polynucleotide encoding ribA polypeptide having an amino acid sequence set out in Table 1 [SEQ ID NO:2 or 4], and polynucleotides that are complementary to such polynucleotides. Alternatively, most highly preferred are polynucleotides that comprise a region that is at least 80% identical over its entire length to a polynucleotide encoding ribA polypeptide and polynucleotides complementary thereto. In this regard, polynucleotides at least 90% identical over their entire length to the same are particularly preferred, and among these particularly preferred polynucleotides, those with at least 95% are especially preferred. Furthermore, those with at least 97% are highly preferred among those with at least 95%, and among these those with at least 98% and at least 99% are particularly highly preferred, with at least 99% being the more preferred.

Preferred embodiments are polynucleotides that encode polypeptides that retain substantially the same biological function or activity as the mature polypeptide encoded by a DNA of Table 1 [SEQ ID NO:1, 3 or 7].

The invention further relates to polynucleotides that hybridize to the herein above-described sequences. In this regard, the invention especially relates to polynucleotides that hybridize under stringent conditions to the herein above-described polynucleotides. As herein used, the terms "stringent conditions" and "stringent hybridization conditions" mean hybridization will occur only if there is at least 95% and preferably at least 97% identity between the sequences. An example of stringent hybridization conditions is overnight incubation at 42° C. in a solution comprising: 50% formamide, 5×SSC (50 mM NaCl, 15 mM trisodium citrate), 150 mM sodium phosphate (pH7.6), 5×Denhardt's solution, 10% dextran sulfate, and 20 micrograms/ml denatured, sheared salmon sperm DNA, followed by washing the hybridization support in 0.1×SSC at about 65° C. Hybridization and wash conditions are well known and exemplified in Sambrook, et al., Molecular Cloning: A Laboratory Manual, Second Edition, Cold Spring Harbor, N.Y., (1989), particularly Chapter 11 therein.

The invention also provides a polynucleotide consisting essentially of a polynucleotide sequence obtainable by screening an appropriate library containing the complete gene for a polynucleotide sequence set forth in SEQ ID NO:1 under stringent hybridization conditions with a probe having the sequence of said polynucleotide sequence set forth in SEQ ID NO:1or a fragment thereof; and isolating said DNA sequence. Fragments useful for obtaining such a polynucleotide include, for example, probes and primers described elsewhere herein.

As discussed additionally herein regarding polynucleotide assays of the invention, for instance, polynucleotides of the invention as discussed above, may be used as a hybridization probe for RNA, cDNA and genomic DNA to isolate full-length cDNAs and genomic clones encoding ribA and to isolate cDNA and genomic clones of other genes that have a high sequence similarity to the ribA gene. Such probes generally will comprise at least 15 bases. Preferably, such probes will have at least 30 bases and may have at least 50 bases. Particularly preferred probes will have at least 30 bases and will have 50 bases or less.

For example, the coding region of the ribA gene may be isolated by screening using a DNA sequence provided in Table 1 [SEQ ID NO: 1, 3 or 7] to synthesize an oligonucleotide probe. A labeled oligonucleotide having a sequence complementary to that of a gene of the invention is then used to screen a library of cDNA, genomic DNA or mRNA to determine which members of the library the probe hybridizes to.

The polynucleotides and polypeptides of the invention may be employed, for example, as research reagents and materials for discovery of treatments of and diagnostics for disease, particularly human disease, as further discussed herein relating to polynucleotide assays.

Polynucleotides of the invention that are oligonucleotides derived from the sequences of Table 1 [SEQ ID NOS:1 or 2 or 3 or 4] may be used in the processes herein as described, but preferably for PCR, to determine whether or not the polynucleotides identified herein in whole or in part are transcribed in bacteria in infected tissue. It is recognized that such sequences will also have utility in diagnosis of the stage of infection and type of infection the pathogen has attained.

The invention also provides polynucleotides that may encode a polypeptide that is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may allow protein transport, may lengthen or shorten protein half-life or may facilitate manipulation of a protein for assay or production, among other things. As generally is the case in vivo, the additional amino acids may be processed away from the mature protein by cellular enzymes.

A precursor protein, having the mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

In addition to the standard A, G, C, T/U representations for nucleic acid bases, the term "N" may also be used in describing certain polynucleotides of the invention. "N" means that any of the four DNA or RNA bases may appear at such a designated position in the DNA or RNA sequence, except it is preferred that N is not a base that when taken in combination with adjacent nucleotide positions, when read in the correct reading frame, would have the effect of generating a premature termination codon in such reading frame.

In sum, a polynucleotide of the invention may encode a mature protein, a mature protein plus a leader sequence (which may be referred to as a preprotein), a precursor of a mature protein having one or more prosequences that are not the leader sequences of a preprotein, or a preproprotein, which is a precursor to a proprotein, having a leader sequence and one or more prosequences, which generally are removed during processing steps that produce active and mature forms of the polypeptide.

Vectors, Host Cells, Expression

The invention also relates to vectors that comprise a polynucleotide or polynucleotides of the invention, host cells that are genetically engineered with vectors of the invention and the production of polypeptides of the invention by recombinant techniques. Cell-free translation systems can also be employed to produce such proteins using RNAs derived from the DNA constructs of the invention.

For recombinant production, host cells can be genetically engineered to incorporate expression systems or portions thereof or polynucleotides of the invention. Introduction of a polynucleotide into the host cell can be effected by methods described in many standard laboratory manuals, such as Davis et al., BASIC METHODS IN MOLECULAR BIOLOGY, (1986) and Sambrook et al., MOLECULAR CLONING: A LABORATORY MANUAL, 2nd Ed., Cold Spring Harbor Laboratory Press, Cold Spring Harbor, N.Y. (1989), such as, calcium phosphate transfection, DEAE-dextran mediated transfection, transvection, microinjection, cationic lipid-mediated transfection, electroporation, transduction, scrape loading, ballistic introduction and infection.

Representative examples of appropriate hosts include bacterial cells, such as streptococci, staphylococci, enterococci *E. coli*, streptomyces and *Bacillus subtilis* cells; fungal cells, such as yeast cells and Aspergillus cells; insect cells such as Drosophila S2 and Spodoptera Sf9 cells; animal cells such as CHO, COS, HeLa, C127, 3T3, BHK, 293 and Bowes melanoma cells; and plant cells.

A great variety of expression systems can be used to produce the polypeptides of the invention. Such vectors include, among others, chromosomal, episomal and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression system constructs may contain control regions that regulate as well as engender expression. Generally, any system or vector suitable to maintain, propagate or express polynucleotides and/or to express a polypeptide in a host may be used for expression in this regard. The appropriate DNA sequence may be inserted into the expression system by any of a variety of well-known and routine techniques, such as, for example, those set forth in Sambrook et al., *MOLECULAR CLONING, A LABORATORY MANUAL*, (supra).

For secretion of the translated protein into the lumen of the endoplasmic reticulum, into the periplasmic space or into the extracellular environment, appropriate secretion signals may be incorporated into the expressed polypeptide. These signals may be endogenous to the polypeptide or they may be heterologous signals.

Polypeptides of the invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography, and lectin chromatography. Most preferably, high performance liquid chromatography is employed for purification. Well known techniques for refolding protein may be employed to regenerate active conformation when the polypeptide is denatured during isolation and or purification.

Diagnostic Assays

This invention is also related to the use of the ribA polynucleotides of the invention for use as diagnostic reagents. Detection of ribA in a eukaryote, particularly a mammal, and especially a human, will provide a diagnostic method for diagnosis of a disease. Eukaryotes (herein also "individual(s)"), particularly mammals, and especially humans, particularly those infected or suspected to be infected with an organism comprising the ribA gene may be detected at the nucleic acid level by a variety of techniques.

Nucleic acids for diagnosis may be obtained from an infected individual's cells and tissues, such as bone, blood, muscle, cartilage, and skin. Genomic DNA may be used directly for detection or may be amplified enzymatically by using PCR or other amplification technique prior to analysis. RNA, cDNA and genomic DNA may also be used in the same ways. Using amplification, characterization of the species and strain of prokaryote present in an individual, may be made by an analysis of the genotype of the prokaryote gene. Deletions and insertions can be detected by a change in size of the amplified product in comparison to the genotype of a reference sequence. Point mutations can be identified by hybridizing amplified DNA to labeled ribA polynucleotide sequences. Perfectly matched sequences can be distinguished from mismatched duplexes by RNase digestion or by differences in melting temperatures. DNA sequence differences may also be detected by alterations in the electrophoretic mobility of the DNA fragments in gels, with or without denaturing agents, or by direct DNA sequencing. See, e.g., Myers et al., *Science*, 230: 1242 (1985). Sequence changes at specific locations also may be revealed by nuclease protection assays, such as RNase and S1 protection or a chemical cleavage method. See, e.g., Cotton et al., *Proc. Natl. Acad. Sci., USA*, 85: 4397–4401 (1985).

Cells carrying mutations or polymorphisms in the gene of the invention may also be detected at the DNA level by a variety of techniques, to allow for serotyping, for example. For example, RT-PCR can be used to detect mutations. It is particularly preferred to used RT-PCR in conjunction with automated detection systems, such as, for example, GeneScan. RNA, cDNA or genomic DNA may also be used for the same purpose, PCR or RT-PCR. As an example, PCR primers complementary to a nucleic acid encoding ribA can be used to identify and analyze mutations. Examples of representative primers are shown below in Table 2.

TABLE 2

Primers for amplification of ribA polynucleotides

| SEQ ID NO | PRIMER SEQUENCE |
|---|---|
| 5 | 5'-ATATGCGCACCAGTGTCTAAAG-3' |
| 6 | 5'-CATCGTGCCGTCATCATTCAT-3' |

The invention also includes primers of the formula:

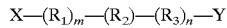

wherein, at the 5' end of the molecule, X is hydrogen, and at the 3' end of the molecule, Y is hydrogen or a metal, $R_1$ and $R_3$ is any nucleic acid residue, m is an integer between 1 and 20 or zero, n is an integer between 1 and 20 or zero, and $R_2$ is a primer sequence of the invention, particularly a primer sequence selected from Table 2. In the polynucleotide formula above $R_2$ is oriented so that its 5' end residue is at the left, bound to $R_1$, and its 3' end residue is at the right, bound to $R_3$. Any stretch of nucleic acid residues denoted by either R group, where m and/or n is greater than 1, may be either a heteropolymer or a homopolymer, preferably a heteropolymer being complementary to a region of a polynucleotide of Table 1. In a preferred embodiment m and/or n is an integer between 1 and 10.

The invention further provides these primers with 1, 2, 3 or 4 nucleotides removed from the 5' and/or the 3' end. These primers may be used for, among other things, amplifying ribA DNA isolated from a sample derived from an individual. The primers may be used to amplify the gene isolated from an infected individual such that the gene may then be subject to various techniques for elucidation of the DNA sequence. In this way, mutations in the DNA sequence may be detected and used to diagnose infection and to serotype and/or classify the infectious agent.

The invention further provides a process for diagnosing, disease, preferably bacterial infections, more preferably infections by *Staphylococcus aureus*, comprising determining from a sample derived from an individual a increased level of expression of polynucleotide having a sequence of Table 1 [SEQ ID NO: 1, 3 or 7]. Increased or decreased expression of ribA polynucleotide can be measured using any on of the methods well known in the art for the quantation of polynucleotides, such as, for example, amplification, PCR, RT-PCR, RNase protection, Northern blotting and other hybridization methods.

In addition, a diagnostic assay in accordance with the invention for detecting over-expression of ribA protein compared to normal control tissue samples may be used to detect the presence of an infection, for example. Assay techniques that can be used to determine levels of a ribA protein, in a sample derived from a host are well-known to those of skill in the art. Such assay methods include radioimmunoassays, competitive-binding assays, Western Blot analysis and ELISA assays.

Antibodies

The polypeptides of the invention or variants thereof, or cells expressing them can be used as an immunogen to produce antibodies immunospecific for such polypeptides. "Antibodies" as used herein includes monoclonal and polyclonal antibodies, chimeric, single chain, simianized antibodies and humanized antibodies, as well as Fab fragments, including the products of an Fab immunolglobulin expression library.

Antibodies generated against the polypeptides of the invention can be obtained by administering the polypeptides or epitope-bearing fragments, analogues or cells to an animal, preferably a nonhuman, using routine protocols. For preparation of monoclonal antibodies, any technique known in the art that provides antibodies produced by continuous cell line cultures can be used. Examples include various techniques, such as those in Kohler, G. and Milstein, C., Nature 256: 495–497 (1975); Kozbor et al., Immunology Today 4: 72 (1983); Cole et al., pg. 77–96 in MONO-CLONAL ANTIBODIES CANCER THERAPY, Alan R. Liss, Inc. (1985).

Techniques for the production of single chain antibodies (U.S. Pat. No. 4,946,778) can be adapted to produce single chain antibodies to polypeptides of this invention. Also, transgenic mice, or other organisms such as other mammals, may be used to express humanized antibodies.

Alternatively phage display technology may be utilized to select antibody genes with binding activities towards the polypeptide either from repertoires of PCR amplified v-genes of lymphocytes from humans screened for possessing anti-ribA or from naive libraries (McCafferty, J. et al., (1990), Nature 348, 552–554; Marks, J. et al., (1992) Biotechnology 10, 779–783). The affinity of these antibodies can also be improved by chain shuffling (Clackson, T. et al., (1991) Nature 352, 624–628).

If two antigen binding domains are present each domain may be directed against a different epitope—termed 'bispecific' antibodies.

The above-described antibodies may be employed to isolate or to identify clones expressing the polypeptides to purify the polypeptides by affinity chromatography.

Thus, among others, antibodies against ribA- polypeptide may be employed to treat infections, particularly bacterial infections.

Polypeptide variants include antigenically, epitopically or immunologically equivalent variants that form a particular aspect of this invention. The term "antigenically equivalent derivative" as used herein encompasses a polypeptide or its equivalent which will be specifically recognized by certain antibodies which, when raised to the protein or polypeptide according to the invention, interfere with the immediate physical interaction between pathogen and mammalian host. The term "immunologically equivalent derivative" as used herein encompasses a peptide or its equivalent which when used in a suitable formulation to raise antibodies in a vertebrate, the antibodies act to interfere with the immediate physical interaction between pathogen and mammalian host.

The polypeptide, such as an antigenically or immunologically equivalent derivative or a fusion protein thereof is used as an antigen to immunize a mouse or other animal such as a rat or chicken. The fusion protein may provide stability to the polypeptide. The antigen may be associated, for example by conjugation, with an immunogenic carrier protein for example bovine serum albumin (BSA) or keyhole limpet haemocyanin (KLH). Alternatively a multiple antigenic peptide comprising multiple copies of the protein or polypeptide, or an antigenically or immunologically equivalent polypeptide thereof may be sufficiently antigenic to improve immunogenicity so as to obviate the use of a carrier.

Preferably, the antibody or variant thereof is modified to make it less immunogenic in the individual. For example, if the individual is human the antibody may most preferably be "humanized"; where the complimentarity determining region(s) of the hybridoma-derived antibody has been transplanted into a human monoclonal antibody, for example as described in Jones, P. et al. (1986), Nature 321, 522–525 or Tempest et al., (1991) Biotechnology 9, 266–273.

The use of a polynucleotide of the invention in genetic immunization will preferably employ a suitable delivery method such as direct injection of plasmid DNA into muscles (Wolff et al., Hum Mol Genet 1992, 1:363, Manthorpe et al., Hum. Gene Ther. 1963:4, 419), delivery of DNA complexed with specific protein carriers (Wu et al., J Biol Chem. 1989: 264,16985), coprecipitation of DNA with calcium phosphate (Benvenisty & Reshef, PNAS USA, 1986:83,9551), encapsulation of DNA in various forms of liposomes (Kaneda et al., Science 1989:243,375), particle bombardment (Tang et al., Nature 1992, 356:152, Eisenbraun et al., DNA Cell Biol 1993, 12:791) and in vivo infection using cloned retroviral vectors (Seeger et al., PNAS USA 1984:81,5849).

Antagonists and agonists—assays and molecules

Polypeptides of the invention may also be used to assess the binding of small molecule substrates and ligands in, for example, cells, cell-free preparations, chemical libraries, and natural product mixtures. These substrates and ligands may be natural substrates and ligands or may be structural or functional mimetics. See, e.g., Coligan et al., Current Protocols in Immunology 1(2): Chapter 5 (1991).

The invention also provides a method of screening compounds to identify those which enhance (agonist) or block (antagonist) the action of ribA polypeptides or polynucleotides, particularly those compounds that are bacteriostatic and/or bactericidal. The method of screening may involve high-throughput techniques. For example, to screen for agonists or antagonists, a synthetic reaction mix, a cellular compartment, such as a membrane, cell envelope or cell wall, or a preparation of any thereof, comprising ribA polypeptide and a labeled substrate or ligand of such polypeptide is incubated in the absence or the presence of a candidate molecule that may be a ribA agonist or antagonist. The ability of the candidate molecule to agonize or antagonize the ribA polypeptide is reflected in decreased binding of the labeled ligand or decreased production of product from such substrate. Molecules that bind gratuitously, i.e., without inducing the effects of ribA polypeptide are most likely to be good antagonists. Molecules that bind well and increase the rate of product production from substrate are agonists. Detection of the rate or level of production of product from substrate may be enhanced by using a reporter system. Reporter systems that may be useful in this regard include but are not limited to calorimetric labeled substrate converted into product, a reporter gene that is responsive to changes in ribA polynucleotide or polypeptide activity, and binding assays known in the art.

Another example of an assay for ribA antagonists is a competitive assay that combines ribA and a potential antagonist with ribA-binding molecules, recombinant ribA binding molecules, natural substrates or ligands, or substrate or ligand mimetics, under appropriate conditions for a competitive inhibition assay. The ribA molecule can be labeled, such as by radioactivity or a colorimetric compound, such that the number of ribA molecules bound to a binding molecule or converted to product can be determined accurately to assess the effectiveness of the potential antagonist.

Potential antagonists include small organic molecules, peptides, polypeptides and antibodies that bind to a polynucleotide or polypeptide of the invention and thereby inhibit or extinguish its activity. Potential antagonists also may be small organic molecules, a peptide, a polypeptide such as a closely related protein or antibody that binds the same sites on a binding molecule, such as a binding molecule, without inducing ribA-induced activities, thereby preventing the action of ribA by excluding ribA from binding.

Potential antagonists include a small molecule that binds to and occupies the binding site of the polypeptide thereby preventing binding to cellular binding molecules, such that normal biological activity is prevented. Examples of small molecules include but are not limited to small organic molecules, peptides or peptide-like molecules. Other potential antagonists include antisense molecules (see Okano, *J. Neurochem.* 56: 560 (1991); *OLIGODEOXYNUCLE-OTIDES AS ANTISENSE INHIBITORS OF GENE EXPRESSION*, CRC Press, Boca Raton, Fla. (1988), for a description of these molecules). Preferred potential antagonists include compounds related to and variants of ribA.

Each of the DNA sequences provided herein may be used in the discovery and development of antibacterial compounds. The encoded protein, upon expression, can be used as a target for the screening of antibacterial drugs. Additionally, the DNA sequences encoding the amino terminal regions of the encoded protein or Shine-Delgarno or other translation facilitating sequences of the respective mRNA can be used to construct antisense sequences to control the expression of the coding sequence of interest.

The invention also provides the use of the polypeptide, polynucleotide or inhibitor of the invention to interfere with the initial physical interaction between a pathogen and mammalian host responsible for sequelae of infection. In particular the molecules of the invention may be used: in the prevention of adhesion of bacteria, in particular gram positive bacteria, to mammalian extracellular matrix proteins on in-dwelling devices or to extracellular matrix proteins in wounds; to block ribA protein-mediated mammalian cell invasion by, for example, initiating phosphorylation of mammalian tyrosine kinases (Rosenshine et al., *Infect. Immun.* 60:2211 (1992); to block bacterial adhesion between mammalian extracellular matrix proteins and bacterial ribA proteins that mediate tissue damage and; to block the normal progression of pathogenesis in infections initiated other than by the implantation of in-dwelling devices or by other surgical techniques.

The antagonists and agonists of the invention may be employed, for instance, to inhibit and treat diseases.

*Helicobacter pylori* (herein *H. pylori*) bacteria infect the stomachs of over one-third of the world's population causing stomach cancer, ulcers, and gastritis (International Agency for Research on Cancer (1994) Schistosomes, Liver Flukes and *Helicobacter Pylori* (International Agency for Research on Cancer, Lyon, France; http://www.uicc.ch/ecp/ecp2904.htm). Moreover, the international Agency for Research on Cancer recently recognized a cause-and-effect relationship between *H. pylori* and gastric adenocarcinoma, classifying the bacterium as a Group I (definite) carcinogen. Preferred antimicrobial compounds of the invention (agonists and antagonists of ribA) found using screens provided by the invention, particularly broad-spectrum antibiotics, should be useful in the treatment of *H. pylori* infection. Such treatment should decrease the advent of *H. pylori*-induced cancers, such as gastrointestinal carcinoma. Such treatment should also cure gastric ulcers and gastritis.

Vaccines

Another aspect of the invention relates to a method for inducing an immunological response in an individual, particularly a mammal which comprises inoculating the individual with ribA, or a fragment or variant thereof, adequate to produce antibody and/or T cell immune response to protect said individual from infection, particularly bacterial infection and most particularly *Staphylococcus aureus* infection. Also provided are methods whereby such immunological response slows bacterial replication. Yet another aspect of the invention relates to a method of inducing immunological response in an individual which comprises delivering to such individual a nucleic acid vector to direct expression of ribA, or a fragment or a variant thereof, for expressing ribA, or a fragment or a variant thereof in vivo in order to induce an immunological response, such as, to produce antibody and/or T cell immune response, including, for example, cytokine-producing T cells or cytotoxic T cells, to protect said individual from disease, whether that disease is already established within the individual or not. One way of administering the gene is by accelerating it into the desired cells as a coating on particles or otherwise. Such nucleic acid vector may comprise DNA, RNA, a modified nucleic acid, or a DNA/RNA hybrid.

A further aspect of the invention relates to an immunological composition which, when introduced into an individual capable or having induced within it an immunological response, induces an immunological response in such individual to a ribA or protein coded therefrom, wherein the composition comprises a recombinant ribA or protein coded therefrom comprising DNA which codes for and expresses an antigen of said ribA or protein coded therefrom. The immunological response may be used therapeutically or prophylactically and may take the form of antibody immunity or cellular immunity such as that arising from CTL or CD4+ T cells.

A ribA polypeptide or a fragment thereof may be fused with co-protein which may not by itself produce antibodies, but is capable of stabilizing the first protein and producing a fused protein which will have immunogenic and protective properties. Thus fused recombinant protein, preferably further comprises an antigenic co-protein, such as lipoprotein D from *Hemophilus influenzae*, Glutathione-S-transferase (GST) or beta-galactosidase, relatively large co-proteins which solubilize the protein and facilitate production and purification thereof. Moreover, the co-protein may act as an adjuvant in the sense of providing a generalized stimulation of the immune system. The co-protein may be attached to either the amino or carboxy terminus of the first protein.

Provided by this invention are compositions, particularly vaccine compositions, and methods comprising the polypeptides or polynucleotides of the invention and immunostimulatory DNA sequences, such as those described in Sato, Y. et al. Science 273: 352 (1996).

Also, provided by this invention are methods using the described polynucleotide or particular fragments thereof which have been shown to encode non-variable regions of bacterial cell surface proteins in DNA constructs used in such genetic immunization experiments in animal models of infection with *Staphylococcus aureus* will be particularly useful for identifying protein epitopes able to provoke a prophylactic or therapeutic immune response. It is believed that this approach will allow for the subsequent preparation of monoclonal antibodies of particular value from the requisite organ of the animal successfully resisting or clearing infection for the development of prophylactic agents or therapeutic treatments of bacterial infection, particularly *Staphylococcus aureus* infection, in mammals, particularly humans.

The polypeptide may be used as an antigen for vaccination of a host to produce specific antibodies which protect against invasion of bacteria, for example by blocking adherence of bacteria to damaged tissue. Examples of tissue damage include wounds in skin or connective tissue caused, e.g., by mechanical, chemical or thermal damage or by implantation of indwelling devices, or wounds in the mucous membranes, such as the mouth, mammary glands, urethra or vagina.

The invention also includes a vaccine formulation which comprises an immunogenic recombinant protein of the invention together with a suitable carrier. Since the protein may be broken down in the stomach, it is preferably administered parenterally, including, for example, administration that is subcutaneous, intramuscular, intravenous, or intradermal. Formulations suitable for parenteral administration include aqueous and non-aqueous sterile injection solutions which may contain anti-oxidants, buffers, bacteriostats and solutes which render the formulation isotonic with the bodily fluid, preferably the blood, of the individual; and aqueous and non-aqueous sterile suspensions which may include suspending agents or thickening agents. The formulations may be presented in unit-dose or multi-dose containers, for example, sealed ampules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

While the invention has been described with reference to certain ribA protein, it is to be understood that this covers fragments of the naturally occurring protein and similar proteins with additions, deletions or substitutions which do not substantially affect the immunogenic properties of the recombinant protein.

Compositions, Kits and Administration

The invention also relates to compositions comprising the polynucleotide or the polypeptides discussed above or their agonists or antagonists. The polypeptides of the invention may be employed in combination with a non-sterile or sterile carrier or carriers for use with cells, tissues or organisms, such as a pharmaceutical carrier suitable for administration to a subject. Such compositions comprise, for instance, a media additive or a therapeutically effective amount of a polypeptide of the invention and a pharmaceutically acceptable carrier or excipient. Such carriers may include, but are not limited to, saline, buffered saline, dextrose, water, glycerol, ethanol and combinations thereof. The formulation should suit the mode of administration. The invention further relates to diagnostic and pharmaceutical packs and kits comprising one or more containers filled with one or more of the ingredients of the aforementioned compositions of the invention.

Polypeptides and other compounds of the invention may be employed alone or in conjunction with other compounds, such as therapeutic compounds.

The pharmaceutical compositions may be administered in any effective, convenient manner including, for instance, administration by topical, oral, anal, vaginal, intravenous, intraperitoneal, intramuscular, subcutaneous, intranasal or intradermal routes among others.

In therapy or as a prophylactic, the active agent may be administered to an individual as an injectable composition, for example as a sterile aqueous dispersion, preferably isotonic.

Alternatively the composition may be formulated for topical application for example in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

For administration to mammals, and particularly humans, it is expected that the daily dosage level of the active agent will be from 0.01 mg/kg to 10 mg/kg, typically around 1 mg/kg. The physician in any event will determine the actual dosage which will be most suitable for an individual and will vary with the age, weight and response of the particular individual. The above dosages are exemplary of the average case. There can, of course, be individual instances where higher or lower dosage ranges are merited, and such are within the scope of this invention.

In-dwelling devices include surgical implants, prosthetic devices and catheters, i.e., devices that are introduced to the body of an individual and remain in position for an extended time. Such devices include, for example, artificial joints, heart valves, pacemakers, vascular grafts, vascular catheters, cerebrospinal fluid shunts, urinary catheters, continuous ambulatory peritoneal dialysis (CAPD) catheters.

The composition of the invention may be administered by injection to achieve a systemic effect against relevant bacteria shortly before insertion of an in-dwelling device. Treatment may be continued after surgery during the in-body time of the device. In addition, the composition could also be used to broaden perioperative cover for any surgical technique to prevent bacterial wound infections, especially *Staphylococcus aureus* wound infections.

Many orthopaedic surgeons consider that humans with prosthetic joints should be considered for antibiotic prophylaxis before dental treatment that could produce a bacteremia. Late deep infection is a serious complication sometimes leading to loss of the prosthetic joint and is accompanied by significant morbidity and mortality. It may therefore be possible to extend the use of the active agent as a replacement for prophylactic antibiotics in this situation.

In addition to the therapy described above, the compositions of this invention may be used generally as a wound treatment agent to prevent adhesion of bacteria to matrix proteins exposed in wound tissue and for prophylactic use in dental treatment as an alternative to, or in conjunction with, antibiotic prophylaxis.

Alternatively, the composition of the invention may be used to bathe an indwelling device immediately before insertion. The active agent will preferably be present at a concentration of 1 µg/ml to 10 mg/ml for bathing of wounds or indwelling devices.

A vaccine composition is conveniently in injectable form. Conventional adjuvants may be employed to enhance the immune response. A suitable unit dose for vaccination is 0.5–5 microgram/kg of antigen, and such dose is preferably administered 1–3 times and with an interval of 1–3 weeks. With the indicated dose range, no adverse toxicological effects will be observed with the compounds of the invention which would preclude their administration to suitable individuals.

Each reference disclosed herein is incorporated by reference herein in its entirety. Any patent application to which this application claims priority is also incorporated by reference herein in its entirety.

GLOSSARY

The following definitions are provided to facilitate understanding of certain terms used frequently herein.

"Disease(s)" means and disease caused by or related to infection by a bacteria, including disease, such as, infections of the upper respiratory tract (e.g., otitis media, bacterial tracheitis, acute epiglottitis, thyroiditis), lower respiratory (e.g., empyema, lung abscess), cardiac (e.g., infective endocarditis), gastrointestinal (e.g., secretory diarrhoea, splenic abscess, retroperitoneal abscess), CNS (e.g., cerebral abscess), eye (e.g., blepharitis, conjunctivitis, keratitis, endophthalmitis, preseptal and orbital cellulitis, darcryocystitis), kidney and urinary tract (e.g., epididymitis, intrarenal and perinephric abscess, toxic shock syndrome), skin (e.g., impetigo, folliculitis, cutaneous abscesses, cellulitis, wound infection, bacterial myositis) bone and joint (e.g., septic arthritis, osteomyelitis).

"Host cell" is a cell which has been transformed or transfected, or is capable of transformation or transfection by an exogenous polynucleotide sequence.

"Identity," as known in the art is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991; and Carillo, H., and Lipman, D., SIAM *J. Applied Math.*, 48: 1073 (1988). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., *Nucleic Acids Research* 12(1): 387 (1984)), BLASTP, BLASTN, and FASTA (Atschul, S. F. et al., *J. Molec. Biol.* 215: 403–410 (1990). The BLAST X program is publicly available from NCBI and other sources (*BLAST Manual*, Altschul, S., et al., NCBI NLM NIH Bethesda, Md. 20894; Altschul, S., et al., *J. Mol. Biol.* 215: 403–410 (1990). As an illustration, by a polynucleotide having a nucleotide sequence having at least, for example, 95% "identity" to a reference nucleotide sequence of SEQ ID NO: 1 it is intended that the nucleotide sequence of the polynucleotide is identical to the reference sequence except that the polynucleotide sequence may include up to five point mutations per each 100 nucleotides of the reference nucleotide sequence of SEQ ID NO: 1. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5 or 3 terminal positions of the reference nucleotide sequence or anywhere between those terminal positions, interspersed either individually among nucleotides in the reference sequence or in one or more contiguous groups within the reference sequence. Analogously, by a polypeptide having an amino acid sequence having at least, for example, 95% identity to a reference amino acid sequence of SEQ ID NO:2 is intended that the amino acid sequence of the polypeptide is identical to the reference sequence except that the polypeptide sequence may include up to five amino acid alterations per each 100 amino acids of the reference amino acid of SEQ ID NO: 2. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

"Isolated" means altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated", as the term is employed herein. Moreover, a polynucleotide or polypeptide that is introduced into an organism by transformation, genetic manipulation or by any other recombinant method is "isolated" even if it is still present in said organism, which organism may be living or non-living.

"Polynucleotide(s)" generally refers to any polyribonucleotide or polydeoxribonucleotide, which may be unmodified RNA or DNA or modified RNA or DNA. "Polynucleotide(s)" include, without limitation, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions. In addition, "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term "polynucleotide(s)" also includes DNAs or RNAs as described above that contain one or more modified bases. Thus, DNAs or RNAs with backbones modified for stability or for other reasons are "polynucleotide(s)" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells. "Polynucleotide(s)" also embraces short polynucleotides often referred to as oligonucleotide(s).

"Polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as proteins. Polypeptides may contain amino acids other than the 20 gene encoded amino acids. "Polypeptide(s)" include those modified either by natural processes, such as processing and other post-translational modifications, but also by chemical modification techniques. Such modifications are well described in basic texts and in more detailed monographs, as well as in a voluminous research literature, and they are well known to those of skill in the art. It will be appreciated that the same type of modification may be present in the same or varying degree at several sites in a given polypeptide. Also, a given polypeptide may contain many types of modifications. Modifications can occur anywhere in a polypeptide, including the peptide backbone, the amino acid side-chains, and the amino or carboxyl termini. Modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation and ADP-ribosylation, selenoylation, sulfation, transfer-RNA mediated addition of amino acids to proteins, such as arginylation, and ubiquitination. See, for instance, *PROTEINS—STRUCTURE AND MOLECULAR PROPERTIES,* 2nd Ed., T. E. Creighton, W. H. Freeman and Company, New York (1993) and Wold, F., Posttranslational Protein Modifications: Perspectives and Prospects, pgs. 1–12 in *POSTTRANSLATIONAL COVALENT MODIFICATION OF PROTEINS,* B. C. Johnson, Ed., Academic Press, New York (1983); Seifter et al., *Meth. Enymol.* 182:626–646 (1990) and Rattan et al., *Protein Synthesis: Posttranslational Modifications and Aging,* Ann. N.Y. Acad. Sci. 663: 48–62 (1992). Polypeptides may be branched or cyclic, with or without branching. Cyclic, branched and branched circular polypeptides may result from post-translational natural processes and may be made by entirely synthetic methods, as well.

"Variant(s)" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques, by direct synthesis, and by other recombinant methods known to skilled artisans.

EXAMPLES

The examples below are carried out using standard techniques, which are well known and routine to those of skill in the art, except where otherwise described in detail. The examples are illustrative, but do not limit the invention.

Example 1

Strain Selection, Library Production and Sequencing

The polynucleotide having a DNA sequence given in Table 1 [SEQ ID NO:1, 3 or 7] was obtained from a library of clones of chromosomal DNA of *Staphylococcus aureus* in *E. coli.* The sequencing data from two or more clones containing overlapping *Staphylococcus aureus* DNAs was used to construct the contiguous DNA sequence in SEQ ID NO: 1. Libraries may be prepared by routine methods, for example:

Methods 1 and 2 below.

Total cellular DNA is isolated from *Staphylococcus aureus* WCUH 29 according to standard procedures and size-fractionated by either of two methods.

Method 1

Total cellular DNA is mechanically sheared by passage through a needle in order to size-fractionate according to standard procedures. DNA fragments of up to 11 kbp in size are rendered blunt by treatment with exonuclease and DNA polymerase, and EcoRI linkers added. Fragments are ligated into the vector Lambda ZapII that has been cut with EcoRI, the library packaged by standard procedures and *E. coli* infected with the packaged library. The library is amplified by standard procedures.

Method 2

Total cellular DNA is partially hydrolyzed with a one or a combination of restriction enzymes appropriate to generate a series of fragments for cloning into library vectors (e.g., RsaI, PalI, AluI, Bshl235I), and such fragments are size-fractionated according to standard procedures. EcoRI linkers are ligated to the DNA and the fragments then ligated into the vector Lambda ZapII that have been cut with EcoRI, the library packaged by standard procedures, and *E. coli* infected with the packaged library. The library is amplified by standard procedures.

Example 2 ribA Characterization

Characterization of *Staphylococcus aureus* ribA Gene Expression

Gene expression in vivo

Recently several novel approaches have been described which purport to follow global gene expression during infection (Chuang, S. et al., (1993); Mahan, M. J. et al., *Science* 259:686–688 (1993); Hensel, M. et al., *Science* 269:400–403 (1995). These new techniques have so far been demonstrated with gram negative pathogen infections but not with infections with gram positives presumably because the much slower development of global transposon mutagenesis and suitable vectors needed for these strategies in these organisms, and in the case of that process described by Chuang, S. et al., *J. Bacteriol.* 175:2026–2036 (1993) the difficulty of isolating suitable quantities of bacterial RNA free of mammalian RNA derived from the infected tissue to furnish bacterial RNA labelled to sufficiently high specific activity.

The present invention employs a novel technology to determine gene expression in the pathogen at different stages of infection of the mammalian host.

Use of the technology of the present invention enables identification of bacterial genes transcribed during infection, inhibitors of which would have utility in anti-bacterial therapy. Specific inhibitors of such gene transcription or of the subsequent translation of the resultant mRNA or of the function of the corresponding expressed proteins would have utility in anti-bacterial therapy.

The determination of expression during infection of a gene from *Staphylococcus aureus* WCUH29

Necrotic fatty tissue from a four day groin infection or kidney from a seven day pyelonephritis infection of *Staphylococcus aureus* WCUH29 in the mouse is efficiently disrupted and processed in the presence of acid phenol and detergent to provide a mixture of animal and bacterial RNA. By freezing the tissue immediately in liquid nitrogen, and processing the tissue samples while still frozen, changes in the population of bacterial mRNA is minimized. The resultant total RNA is free of DNA and protein (including RNAases and DNAases). The optimal conditions for disruption and processing to give high yields of bacterial mRNA with transcripts of long length are followed by reverse transcribing the resulting mRNA to cDNA and amplified with ORF-specific primers for a bacterial gene known to be expressed constitutively and at low copy number in *Staphylococcus aureus* WCUH29. Aspects of this example II, part b, are modifications of a published protocol (Cheung, et al.; Anal Biochem (1994) 222:511–514).

a) Isolation of tissue infected with *Staphylococcus aureus* WCUH29 from murine models of infection i) Isolation of tissue infected with *Staphylococcus aureus* WCUH29 from a murine thigh lesion model of infection. 10 ml. volumes of sterile nutrient broth (No.2 Oxoid) are seeded with isolated, individual colonies of *Staphylococcus aureus* WCUH29 from an agar culture plate. The cultures are incubated aerobically (static culture) at 37° C. for 16–20 hours. 4 week old mice (female, 18 g–22 g, strain MF1) are each infected by subcutaneous injection of 0.5 ml. of this broth culture of *Staphylococcus aureus* WCUH29 (diluted in broth to approximately $10^8$ cfu/ml.) into the anterior, right lower quadrant (groin area). Mice should be monitored regularly during the first 24 hours after infection, then daily until termination of study. Animals with signs of systemic infection, i.e. lethargy, ruffled appearance, isolation from group, should be monitored closely and if signs progress to moribundancy, the animal should be culled immediately.

Visible external signs of lesion development will be seen 24–48 h after infection. Examination of the abdomen of the animal will show the raised outline of the abscess beneath the skin. The localised lesion should remain in the right lower quadrant, but may occasionally spread to the left lower quadrant, and superiorly to the thorax. On occasions, the abscess may rupture through the overlying skin layers. In such cases the affected animal should be culled immediately and the tissues sampled if possible. Failure to cull the animal may result in the necrotic skin tissue overlying the abscess being sloughed off, exposing the abdominal muscle wall.

Approximately 96 hours after infection, animals are killed using carbon dioxide asphyxiation. To minimise delay between death and tissue processing /storage, mice should be killed individually rather than in groups. The dead animal is placed onto its back and the fur swabbed liberally with 70% alcohol. An initial incision using scissors is made through the skin of the abdominal left lower quadrant, travelling superiorly up to, then across the thorax. The incision is completed by cutting inferiorly to the abdominal lower right quadrant. Care should be taken not to penetrate the abdominal wall. Holding the skin flap with forceps, the skin is gently pulled way from the abdomen. The exposed abscess, which covers the peritoneal wall but generally does not penetrate the muscle sheet completely, is excised, taking care not to puncture the viscera The abscess/muscle sheet and other infected tissue may require cutting in sections, prior to flash-freezing in liquid nitrogen, thereby allowing easier storage in plastic collecting vials.

ii) Isolation of tissue infected with *Staphylococcus aureus* WCUH29 from a murine model of hematogenous pyelonephritis. Overnight cultures of *S. aureus* WCUH29 were started from single colonies in 5 ml of tryptic soy broth (TSB) and grown at 37° C. with shaking. The cultures were then washed twice in sterile phosphate-buffered saline (PBS) and diluted to an A600=0.3. Male CD-1 mice (18–20 g) were infected with 0.2 ml of this suspension by tail vein inoculation using a 30 g needle attached to a tuberculin syringe. Each mouse receives approximately $4 \times 10^7$ bacteria in this fashion. Mice are monitored daily for signs of illness, and usually within 48 hours show signs of lethargy, ruffled fur, sluggishness; animals which appear moribund are euthanized prior to the end of the experiment.

All animals are euthanized via carbon dioxide overdose seven days post-infection. The animal is placed on its back and swabbed with ethanol, and then with RNAZap, and instruments are swabbed as well. The abdominal cavity is opened and the kidneys aseptically removed, cut into four pieces, and placed in cryovials which are immediately frozen in liquid nitrogen.

b) Isolation of *Staphylococcus aureus* WCUH29 RNA from infected tissue samples

Infected tissue samples, in 2-ml cryo-strorage tubes, are removed from liquid nitrogen storage for immediate processing of the frozen tissue. In a microbiological safety cabinet the samples are disrupted up to eight at a time. To disrupt the bacteria within the tissue sample, 50–100 mg of the tissue is transfered to a FastRNA tube containing a silica/ceramic matrix (BIO101). Immediately, 1 ml of extraction reagents (FastRNA reagents, BIO101) are added to give a sample to reagent volume ratio of approximately 1 to 20. The tubes are shaken in a reciprocating shaker (FastPrep FP120, BIO101) at a setting of 5.5 to 6 for 20–120 sec. The crude RNA preparation is extracted with chloroform/isoamyl alcohol, and precipitated with DEPC-treated/Isopropanol Precipitation Solution (BIO101). RNA preparations are stored in this isopropanol solution at −80° C. if necessary. The RNA is pelleted (12,000 g for 10 min.), washed with 75% ethanol (v/v in DEPC-treated water), air-dried for 5–10 min, and resuspended in 0.1 ml of DEPC-treated water.

Quality of the RNA isolated is assessed by the ability to detect bacterial transcripts up to 2 kb in length by RT-PCR (as described in section below). To demonstrate the isolation of bacterial RNA from the infected tissue, samples of RNA are reverse transcribed, and the presence of a constitutively expressed gene is detected through the use of quantitative PCR in the presence of a TaqMan probe (as described below).

c) The removal of DNA from *Staphylococcus aureus* WCUH29-derived RNA

DNA was removed from 50 microgram samples of RNA by a 30 minute treatment at 37° C. with 10 units of RNAase-free DNAaseI (GeneHunter) in the buffer supplied in a final volume of 57 microliters.

The DNAase was inactivated and removed by phenol:chloroform extraction. RNA was precipitated with 5 microliters of 3 M NaOAc and 200 microliters 100% EtOH, and pelleted by centrifugation at 12,000 g for 10 minutes. The RNA is pelleted (12,000 g for 10 min.), washed with 75% ethanol (v/v in DEPC-treated water), air-dried for 5–10 min, and resuspended in 10–20 microliters of DEPC-treated water. RNA yield is quantitated by $OD_{260}$ after 1:1000 dilution of the cleaned RNA sample. RNA is stored at −80° C. if necessary and reverse-transcribed within one week.

d) The preparation of cDNA from RNA samples derived from infected tissue 10 microliter samples of DNAase treated RNA are reverse transcribed using a SuperScript Preamplification System for First Strand cDNA Synthesis kit (Gibco BRL, Life Technologies) according to the manufacturers instructions. 1 nanogram of random hexamers is used to prime each reaction. Controls without the addition of SuperScriptII reverse transcriptase are also run. Both +/−RT samples are treated with RNaseH before proceeding to the PCR reaction.

e) The use of PCR to determine the quality of bacterial RNA derived from infected tissue Long transcripts, which are expected to be of low copy number within the bacterial cell, such as penicillin-binding protein 2 (PBP2), are reverse transcribed with random primers as described above and amplified by the following PCR method using ORF-specific primers, in order to ascertain the quality, represented by length amplified, of the mRNA obtained during extraction and purification.

PCR reactions are set up on ice in 0.2 ml tubes in a total volume of 50 ul by adding the following components [final concentration]: AmpliTaq PCR Buffer II (1×), 1.5 mM $MgCL_2$, 1 mM dNTPs, 0.5 uM forward primer, 0.5 uM reverse primer, and 2 ul reverse-transcribed RNA. PCR reactions are run on a PE GeneAmp PCR System 9600 with an initial step of 94° C. for 2 min, followed by 35 cycles of 94° C. for 30 sec, 42° C. for 30 sec and 72° C. for 30 sec, followed by a final extensison at 72° C. for 7 min.

f) The use of PCR to determine the presence of a bacterial cDNA species

PCR reactions are set up as described above using 0.5 microM each of the ORF specific forward and reverse primers.

PCR product in 20 microliter aliquots are separated by electrophoresis through 1 to 1.5% 1×TBE agarose gels or 10% 1×TBE acrylamide gels. PCR product is visualized by staining the gel with ethidium bromide. Size estimates are made by comparison to a 100 bp DNA Ladder (Gibco BRL, Life Technologies). Alternatively, if the PCR products are conveniently labelled by the use of a labelled PCR primer (e.g. labelled at the 5'end with a dye) a suitable aliquot of the PCR product is run out on a polyacrylamide sequencing gel and its presence and quantity detected using a suitable gel scanning system (e.g. ABI Prism™ 377 Sequencer using GeneScan™ software as supplied by Perkin Elmer).

RT/PCR controls may include +/− reverse transcriptase reactions, 16 s rRNA primers or DNA specific primer pairs designed to produce PCR products from non-transcribed *Staphylococcus aureus* WCUH29 genomic sequences.

To test the efficiency of the primer pairs they are used in DNA PCR with *Staphylococcus aureus* WCUH29 total DNA. PCR reactions are set up and run as described above using approx. 1 microgram of DNA in place of the cDNA and 35 cycles of PCR.

Primer pairs which fail to give the predicted sized product in either DNA PCR or RT/PCR are PCR failures and as such are uninformative. Of those which give the correct size product with DNA PCR two classes are distinguished in RT/PCR: 1.Genes which are not transcribed in vivo reproducibly fail to give a product in RT/PCR; and 2.Genes which are transcribed in vivo reproducibly give the correct size product in RT/PCR and show a stronger signal in the +RT samples than the signal (if at all present) in −RT controls.

g) The use of PCR and fluorogenic probes to determine the presence of a bacterial cDNA species Specific sequence detection occurs by amplification of target sequences in the PE Applied Biosystems 7700 Sequence Detection System in the presence of an oligonucleotide probe labeled at the 5' and 3' ends with a reporter and quencher fluorescent dye, respectively (FQ probe), which anneals between the two PCR primers. Only specific product will be detected when the probe is bound between the primers. As PCR amplification proceeds, the 5'-nuclease activity of Taq polymerase initially cleaves the reporter dye from the probe. The signal generated when the reporter dye is physically separated from the quencher dye is detected by measuring the signal with an attached CCD camera. Each signal generated equals one probe cleaved which corresponds to amplification of one target strand PCR reactions are set up using the PE Applied Biosystem TaqMan PCR Core Reagent Kit according to the instructions supplied such that each reaction contains 5 microliters 10×PCR Buffer II, 7 microliters 25 mM $MgCl_2$, 5 microliters 300 nM forward primer, 5 microliters reverse primer, 5 microliters specific FQ probe, 1 microliter each 10 mM dATP, 10 mM dCTP, 10 mM dGTP and 20 mM dUTP, 13.25 microliters distilled water, 0.5 microliters AmpErase UNG, and 0.25 microliters AmpliTaq DNA polymerase to give a total volume of 45 microliters.

Amplification proceeds under the following thermal cycling conditions: 50° C. hold for 2 minutes, 95° C. hold for 10 minutes, 40 cycles of 95° C. for 15 seconds and 60° C. for 1 minute, followed by a 25° C. hold until sample is retrieved. Detection occurs real-time. Data is collected at the end of the reaction.

Based on these analyses it was discovered that the *Staphylococcus aureus* ribA gene was transcribed in vivo.

Riboflavin Biosynthesis Operon

This ORF is part of an operon which encodes genes ribG, ribB, ribA and ribH. Gene ribG starts at nucleotide 1 and ends at nucleotide 1029. Gene ribB starts at nucleotide 1036 and ends at nucleotide 1668. Gene ribA starts at nucleotide 1679 and ends at nucleotide 2860.

Gene ribH starts at nucleotide 2873 and ends at nucleotide 3337. This operon [SEQ ID NO: 7] is as follows:

ATGGATTATGCGATTCAACTTGCAAATATGGTACAAGGTCAAACAGGTGTTAATCCACCCGTTGGCGCTG
TTGTAGTTAATGAAGGTAGGATTGTTGGTATTGGTGCACACTTGAGAAAAGGTGACAAGCATGCGGAGGT
TCAAGCACTTGATATGGCACAACAAAATGCTGAAGGTGCGACGATTTATATTACGTTAGAGCCATGTAGT
CATTTTGGTTCAACACCACCCTGTGTTAACAAAATTATTGATTGTAAGATAGCAAAAGTAGTATACGCAA
CAAAAGACAATTCGTTAGACACACATGGTGATGAGACGTTACGGGCTCACGGTATTGAGGTTAATGCGT
TGATGATGAACGGGCATCACAATTATACCAAGACTTTTTTAAAGCAAAAGCAAAGCAACTGCCACAAATT
ACAGTGAAAGTATCTGCAAGTTTAGATGGTAAACAAGCGAATGATAATGGACAAAGTCAATGGATTACTA
ACAAAGAGGTTAAACAAGATGTCTATAAGTTAAGACATCGACACGACGCAGTGTTAACTGGAAGACGTAC
AGTTGAATTAGATGATCCACAATATACTACACGTATTCAAGATGGAAAAAACCCTATAAAAGTAATATTG
TCTAAGTCTGGGAATATTCATTTTAATCAGCAAATTTATCAAGATGAATCAACACCAATTTGGATATATA
CTGAAAATCCAAATTTAACAAGCAATCAAACACATATTGAAATTATTTACTTGAAGTCTTGTGATTTAAC
AACAATTCTTCACAATTTATATAAAAGAGGAGTTGGAACTTTGCTAGTCGAGGCAGGTCCAACCACTACT
TCAGAATTCTCCATCTATTATATAGATGAATTTATTCTCTATTATGCCCCGAAATTAATTGGCGGATCTG
GAAATTATCAATTTTATCAAACAAATGATGTGATTGAGATACCAGATGCGAACCAATTTGAAATTGTTCA
TTCCGAGTTATTAAATCAAAATGTTAAATTAACTTTACGAAAGAAGTGATGATGCATGTTTACTGGCATC
GTTGAAGAAATAGGTGTCGTTAAAAGTGTTCAAATTCGTCAATCAGTCAGGACGATTGAAATCGAAGCAC
ATAAGATTACGGCAGATATGCATATTGGTGATTCCATCAGTGTTAATGGTGCATGTTTAACAGTGATTGA
TTTTGATCAGACATCTTTTACTGTTCAAGTAATTAAAAGCACTGAAAATAAAACCTATTTAGCAGATGTT
AAGCGACAATCAGAAGTAAATTTAGAGCGTGCCATGAGTGGTAACGGTAGGTTTGGTGGACATTTTGTCC
TCGGTCATGTAGATGAACTAGGAACAGTTT
CAAAAATAAATGAAACAGCCAATGCCAAAATTATTACGATTCAATGTAGCCAACATATTAATAATCAGTT
AGTTAAGCAAGGGTCTATTACTGTGGATGGTGTAAGTCTAACGGTATTTGATAAGCATGATAACAGTTTT
GACATTCATCTTATTCCAGAAACGAGGCGTTCAACGATTTTATCATCCAAAAAATTAGGAGATAAAGTAC
ATTTAGAAACAGACGTTTTGTTTAAATATGTTGAAAATATTTTAAATAAAGATAAAGACCAATTATCTGT
AGATAAATTAAGAGCATTTGGTTTTTAGGAGGGGTAGCATGCAATTCGATAATATTGACAGTGCTTTAAT
GGCTTTAAAAAATGGAGAAACAATTATTGTAGTAGATGATGAGAATCGTGAAAATGAAGGTGATTTAGTA
GCGGTTACTGAATGGATGAACGATAATACCATTAATTTTATGGCGAAAGAAGCAAGGGGATTAATATGCG
CACCAGTGTCTAAAGATATTGCACAACGTTTGGATTTGGTACAAATGGTTGATGATAACTCCGACATCTT
TGGTACGCAATTTACAGTGAGTATTGATCATGTAGATACAACAACAGGAATTAGTGCTTATGAACGTACA
TTGACTGCCAAAAAGCTCATTGATCCTAGTAGTGAAGCTAAAGATTTTAATCGTCCTGGTCATTTATTTC
CATTAGTAGCACAAGATAAAGGCGTATTAGCTAGAAATGGACACACAGAAGCGGCTGTTGATTTAGCTAA
ACTTACTGGTGCCAAGCCCGCTGGTGTCATTTGTGAGATTATGAATGATGACGGCACGATGGCGAAAGGA
CAAGATTTACAAAATTTTAAAGAAAAACATCAATTAAAGATGATTACGATTGATGATTTAATTGAATATC
GTAAAAAATTAGAACCAGAAATTGAATTTAAGGCAAAAGTGAAAATGCCTACAGATTTCGGAACATTTGA
TATGTATGGTTTTAAAGCGACATACACAGATGAAGAGATAGTTGTACTGACAAAAGGTGCAATTCGACAA
CATGAAAATGTACGCTTACATTCTGCGTGCCTTACAGGCGATATTTTCCATAGTCAACGTTGTGATTGTG
GTGCTCAACTTGAATCGTCTATGAAGTATATCAATGAACATGGTGGCATGATTATTTATCTACCTCAAGA
AGGTCGTGGCATAGGATTGTTAAACAAATTACGCGCATATGAATTAATTGAGCAAGGATATGATACAGTA
ACTGCAAATTTAGCATTAGGTTTTGATGAAGATTTACGAGATTATCATATTGCTGCACAGATTTTAAAAT
ATTTTAACATCGAACATATCAATTTATTAAGTAATAATCCAAGTAAATTTGAGGGATTAAAACAATATGG

-continued

```
CATTGATATTGCAGAAAGAATTGAAGTTATCGTACCAGAAACGGTACATAATCATGATTATATGGTAACG

AAAAAAATAAAAATGGGTCATTTAATATAGGAGGACTTTAACATGAATTTTGAAGGTAAATTAATTGGAA

AAGATTTGAAAGTTGCAATCGTAGTTAGTCGATTTAATGATTTTATCACTGGAAGATTACTTGAAGGTGC

AAAAGATACTTTGATTCGACATGATGTTAATGAAGACAATATTGATGTAGCATTTGTTCCTGGTGCGTTT

GAAATTCCTTTAGTAGCTAAAAAATTAGCCTCATCAGGAAATTATGATGCAATAATTACATTAGGATGCG

TAATTCGCGGTGCTACGTCTCATTATGATTATGTTTGTAATGAAGTGCGAAAGGTGTTTCTAAAGTAAAT

GATCAAACTAATGTACCAGTCATATTTGGTATTTTAACGACTGAAAGTATTGAACAAGCTGTGGAAAGAG

CAGGTACGAAAGCTGGTAATAAAGGTGCCGAAGCAGCAGTAAGTGCAATTGAAATGGCTAATTTATTAAA

ATCTATAAAAGCATAG
```

What is claimed is:

1. An isolated polypeptide comprising the amino acid sequence set forth in SEQ ID NO:2.

2. A composition comprising the isolated polypeptide of claim 1 and a carrier.

3. The isolated polypeptide of claim 1, wherein the isolated polypeptide comprises a heterologous amino acid sequence fused to the amino acid sequence set forth in SEQ ID NO:2.

4. A composition comprising the isolated polypeptide of claim 3 and a carrier.

5. The isolated polypeptide of claim 1, wherein the isolated polypeptide consists of the amino acid sequence set forth in SEQ ID NO:2.

6. A composition comprising the isolated polypeptide of claim 5 and a carrier.

7. An isolated polypeptide comprising at least 50 consecutive amino acids of SEQ ID NO:2.

8. A composition comprising the isolated polypeptide of claim 7 and a carrier.

9. The isolated polypeptide of claim 7, wherein the isolated polypeptide comprises a heterologous amino acid sequence fused to the at least 50 consecutive amino acids of SEQ ID NO:2.

10. A composition comprising the isolated polypeptide of claim 9 and a carrier.

11. An isolated polypeptide comprising at least 30 consecutive amino acids of SEQ ID NO:2.

12. A composition comprising the isolated polypeptide of claim 11 and a carrier.

13. The isolated polypeptide of claim 11, wherein the isolated polypeptide comprises a heterologous amino acid sequence fused to the at least 30 consecutive amino acids of SEQ ID NO:2.

14. A composition comprising the isolated polypeptide of claim 13 and a carrier.

* * * * *